United States Patent [19]

Stab et al.

[11] Patent Number: 5,494,676
[45] Date of Patent: Feb. 27, 1996

[54] DERMATOLOGICAL COMPOSITIONS CONTAINING CIS-UROCANINIC ACID

[75] Inventors: Franz Stab, Echem; Udo Hoppe, Hamburg; Gerhard Sauermann, Wiemersdorf; Walter Engel, Pinneberg, all of Germany

[73] Assignee: Bode Chemie, Hamburg, Germany

[21] Appl. No.: 443,970

[22] Filed: May 18, 1995

Related U.S. Application Data

[62] Division of Ser. No. 254,451, Jun. 6, 1994, Pat. No. 5,455,036, which is a continuation of Ser. No. 7,448, Jan. 22, 1993, abandoned, which is a continuation-in-part of Ser. No. 722,062, Jun. 27, 1991, abandoned.

[30] Foreign Application Priority Data

Jun. 29, 1990 [DE] Germany ............................ 40 20 739.0

[51] Int. Cl.$^6$ ............................ A61K 31/195; A61K 7/40
[52] U.S. Cl. ............................ 424/401; 424/59; 424/60; 514/861
[58] Field of Search ............................ 424/401, 59, 60; 514/861

[56] References Cited

U.S. PATENT DOCUMENTS

| | | | |
|---|---|---|---|
| 4,181,804 | 1/1980 | Mecca | 424/59 |
| 4,419,343 | 12/1983 | Pauly | 424/59 |
| 4,424,234 | 1/1984 | Alderson et al. | 514/784 |
| 4,897,260 | 1/1990 | Ross et al. | 424/59 |
| 5,011,855 | 4/1991 | Traitler et al. | 514/558 |
| 5,045,559 | 9/1991 | Scott | 514/423 |

FOREIGN PATENT DOCUMENTS 9422441  10/1994  WIPO.

OTHER PUBLICATIONS

Scott et al., "Histidine—Rich Protein . . . Stratum Corneum". Biochimica Et Biophysica Acta, 719: pp. 110–117 (1982).

"Urocanic Acid Analogues . . . Herpes Simplex Virus" Norval et al, Photochem–Photobiology, 1989 May, 49(5): pp. 633–639.

Primary Examiner—Melvyn I. Marquis
Assistant Examiner—Robert H. Harrison
Attorney, Agent, or Firm—Sprung Horn Kramer & Woods

[57] ABSTRACT

Dermatological compositions having an effective content of cis-urocaninic acid and/or its derivatives, the process for the produktion of such compositions and the method of use of dermatological compositions having a content of cis-urocaninic acid for the treatment and the prophylaxis of inflammatory dermatoses and for the care and restoration of senstive and stressed skin.

6 Claims, No Drawings

DERMATOLOGICAL COMPOSITIONS CONTAINING CIS-UROCANINIC ACID

This is a division of Application Serial No. 08/254,451, filed on Jun. 6, 1994, U.S. Pat. No. 5,455,036, which is a continuation of application Ser. No. 08/007,448 filed on Jan. 22, 1993, now abandoned, which is a continuation in part of Ser. No. 07/722,062 filed on Jun. 27, 1991, now abandoned.

The present invention relates to products for the treatment and especially for the prophylaxis of inflammatory or allergic dermatoses and for the care and restoration of sensitive or stressed skin. The present invention further relates to preparations for topical application.

Dermatoses produce a great burden of suffering on the affected. The number of inflammatory or allergic dermatoses is continuously increasing in the industrialized countries. Investigations confirm that occupationally related skin disorders obviously play a substantial role here. Occupational dermatoses are especially of existential importance for the affected persons, since in many cases they force a change of occupation. At the least, however, they require increased precautionary measures.

Most common widespread are metal allergies, particularly allergies to heavy metals, such as nickel, copper and chromium.

Since, in many states of the world, many coins essentially consist of nickel alloys, avoiding the contact to nickel proves nearly impossible. Prophylaxis, healing or at least relief of nickel allergy is, therefore, an important aim of the present invention.

Products for the treatment of these disorders are known per se, and antihistaminics or glucocorticoids are employed in particular. For prophylaxis, on the other hand, no suitable preparations are hitherto known.

However, the compositions of prior art, which in the meantime are employed in many commercial forms, have some disadvantages: in many people, antihistaminics cause languor and drowsiness. Permanent use of glucocorticoids (for example cortisone) is usually unjustifiable for medical reasons owing to many unpleasant side effects. The same also applies to most so-called NSAID (non-steroidal anti-inflammatory drugs).

It was thus the object of the present invention to find ways to avoid the disadvantages of the prior art. In particular, it was intended to make agents available which can be employed effectively for the treatment and prophylaxis of inflammatory or allergic dermatoses and for the care and restoration of sensitive or stressed skin without the side effects described occuring.

According to the invention these objects are achieved by dermatological compositions for the treatment or prophylaxis of psoriasis, allergies, particularly allergies to heavy metals, neurodermatitis and for the care and restoration of sensitive or stressed skin, said compositions having an effective content of cis-urocaninic acid and/or its dermatologically or pharmaceutically acceptable salts.

cis-Urocaninic acid (also known as cis-urocanic acid or cis-4-imidazolylacrylic acid) is characterized by the following structural formula:

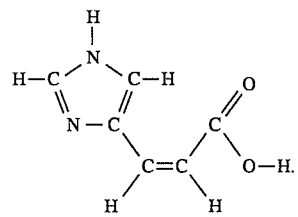

It has the molecular formula $C_6H_6N_2O_2$ and the molecular weight 138,12. cis-Urocaninic acid is formed, for example by UV irradiation of the trans-isomer, which occurs in human skin and also in perspiration. The use of the trans-isomer as a sunscreen is known.

It has been shown in the most highly surprising way that cis-urocaninic acid has an anti-inflammatory action, alleviates the consequences of allergic reactions and to a great extent prevents allergic reactions.

Because of these anti-inflammatory and anti-allergic power the compositions according to the invention are active against psoriasis, neurodermatitis and contact dermatitis.

It is supposed that at least some of the advantageous effects of urocaninic acid can be interpreted as being due to sequestering of small molecules or ions by urocanic acid. It has been proved by experiments that metal ions, in particular heavy metal ions such as $Ni^{2+}$, $Cr^{3+}$, $Co^{2+}$, $Co^{3+}$ and $Cu^{2+}$, are sequestered by cis-urocaninic acid in form of complexes.

Nocuous small molecules or ions being sequestered by cis-urocaninic acid in dermatological formulations is thus another feature of the present invention.

In the compositions according to the invention the cis-urocaninic acid is preferably present in concentrations of 0.00001 mg/ml–60 mg/ml. Preferred are compositions having concentrations of 0.01 mg/ml–2.0 mg/ml, especially those of 0.05 mg/ml–1.0 mg/ml.

The compositions according to the present invention are applied topically, on the skin of the patient. Preferred are several applications a day over a period and in quantities sufficient to give alleviation to the affected person, for example 14 days.

The compositions according to the present invention are equally applied topically, on the skin of the patient, if prophylaxis is intended. Preferred are several applications a day over a period and in sufficient quantities to the patient, for example 14 days.

cis-Urocaninic acid-containing formulations according to the invention can advantageously be selected from all commercial forms, for example creams, gels, lotions, sprays, milks etc. It has proved favorable to incorporate aqueous or alcoholic/aqueous or alcoholic or acetone/aqueous or acetone or acetone/alcoholic solutions of cis-urocaninic acid in the formulations.

It is furthermore advantageous to dilvants auxiliaries and/or additives in the compositions, which increase the stability of cis-urocaninic acid or its derivatives or which improve or modify the quality of the compositions from the pharmaceutical viewpoint.

Auxiliaries and additives are, for example, thickeners, fillers, colorants, emulsifiers, additional active compounds such as lightscreens, stabilizers, antioxidants, preservatives, alcohol, water, salts, substances having proteolytic or keratolytic activity etc.

It is especially advantageous to add unsaturated fatty acids to the compositions according to the invention, since these increase the effect of the cis-urocaninic acid further in a surprising way. Preferred acids here are gamma-linolenic acid, eicosapentaenoic acid, docosahexaenoic acid, oleic acid and their derivatives, advantageously the corresponding esters and salts. The unsaturated acids or the corresponding derivatives are preferably present in concentrations of 0.2–2.0% by weight, related to the entire weight of the composition.

It is perfectly convenient to use mixtures of cis- and trans-urocaninic acid. The effect according to the invention here indeed emanates from the cis-compound, but the user can make use of the properties, e.g. light-protecting properties, of the trans-compound as well.

In particular, it is also advantageous to expose trans-urocaninic acid to ultraviolet radiation, whereupon a mixture of cis- and trans-isomers is formed, and to incorporate this mixture into the appropriate formulation.

Otherwise, the customary measures which are known to the person skilled in the art are to be observed.

The following examples are used to describe the invention without it being intended to restrict the invention to these examples. cis-urocaninic acid is abbreviated in the examples as UCA.

EXAMPLE 1

Aqueous preparation (face lotion)

| | % by weight |
|---|---|
| PEG-40-hydrogenated Castor Oil | 0.811 |
| Dipropylenglycol | 2.534 |
| PEG-8 | 1.521 |
| Na₃EDTA | 0.253 |
| Polymer JR 125 | 0.025 |
| UCA | 0.750 |
| Water demin. | to 100.000 |

EXAMPLE 2

Aqueous composition

| | % by weight |
|---|---|
| Polyfatty acid ester (Cetiol HE) | 16.000 |
| PPG-3-myristyl ether (Witconol APM) | 1.000 |
| Propylene glycol | 3.000 |
| Glycerol | 40.000 |
| UCA | 0.500 |
| Water demin. | to 100.000 |

EXAMPLE 3

Hydrogel (Polyacrylate gel)

| | % by weight |
|---|---|
| Acrylic acid polymer (Carbopol 934) | 1.000 |
| Tris(hydroxymethylamino)methane (Tris) | 1.000 |
| Glycerol | 2.000 |
| Propylene glycol | 2.000 |
| UCA | 0.050 |
| Water demin. | to 100.000 |

EXAMPLE 4

Preparation having a high water content (very soft)

| | % by weight |
|---|---|
| Ceteareth (Cremophor A 25) | 0.100 |
| Cetearyl Alcohol (Lanette O) | 0.400 |
| Petroleum jelly GP 9 | 12.500 |
| Mineral Oil GP 9 | 11.000 |
| Ceteareth-6-stearyl alcohol (Cremophor A6) | 6.000 |
| UCA | 0.020 |
| Water demin. | to 100.000 |

EXAMPLE 5

Preparation having a high water content (soft)

| | % by weight |
|---|---|
| Ceteareth-25 (Cremophor A25) | 1.500 |
| Cetearyl Alcohol (Lanette O) | 8.500 |
| UCA | 0.250 |
| Water demin. | to 100.000 |

EXAMPLE 6

Preparation having a high water content (soft)

| | % by weight |
|---|---|
| Ceteareth-25 (Cremophor A25) | 2.000 |
| Cetearyl alcohol (Lanette O) | 8.000 |
| Petroleum jelly, GP 9 | 10.000 |
| Mineral Oil, GP 9 | 10.000 |
| UCA | 0.100 |
| Water demin. | to 100.000 |

EXAMPLE 7

Preparation having a high water content (semisolid)

| | % by weight |
|---|---|
| Ceteareth-25 | 3.000 |
| Cetearyl Alcohol (Lanette O) | 17.000 |
| UCA | 0.175 |
| Water demin. | to 100.000 |

EXAMPLE 8

Watery lotion

| | % by weight |
|---|---|
| Ceteareth-25 (Cremophor A25) | 1.000 |
| Ceteareth-6-stearyl alcohol (Cremophor A6) | 1.000 |
| Glycerol-mono-distearate (Tegin normal) | 2.000 |
| Cetyl alcohol | 1.000 |
| Isopropyl myristate | 1.450 |
| Glycerol | 1.000 |
| Polyvinylpyrrolidone | 0.500 |
| UCA | 0.125 |

-continued

|  | % by weight |
|---|---|
| Water demin. | to 100.000 |

EXAMPLE 9

Viscous lotion

|  | % by weight |
|---|---|
| Ceteareth 25 (Cremophor A25) | 2.000 |
| Cetearyl Alcohol (Lanette O) | 3.000 |
| Mineral Oil, GP 9 | 5.000 |
| Propylene glycol | 3.000 |
| Polyvinylpyrrolidone | 0.500 |
| UCA | 0.300 |
| Water demin. | to 100.000 |

EXAMPLE 10

W/O-Cream

|  | % by weight |
|---|---|
| Glycerol sorbitan fatty acid ester (Arlacel 481) | 6.000 |
| Mikrocrystalline Wax (Lunacera M) | 1.000 |
| Neutral Oil | 3.000 |
| Paraffin Oil | 19.000 |
| Magnesium stearate | 1.000 |
| Propylene glycol | 3.700 |
| Magnesium sulphate (MgSO$_4$*7 H$_2$O) | 0.700 |
| UCA | 1.000 |
| Water demin. | to 100.000 |

EXAMPLE 11

W/O-Emulsion

|  | % by weight |
|---|---|
| Polyoxyethylene glycerol sorbitan fatty acid ester (Arlacel 988) | 3.600 |
| Polyoxyethylene fatty acid ester (Arlacel 989) | 1.400 |
| Cetearyl Alcohol (Lanette O) | 2.000 |
| Mineral Oil, GP 9 | 25.000 |
| Paraben mixture | as desired |
| Magnesium sulphate (MgSO$_4$*7 H$_2$O) | 0.700 |
| UCA | 1.250 |
| Water demin. | to 100.000 |

EXAMPLE 12

W/O-Lotion

|  | % by weight |
|---|---|
| Glycerol sorbitan fatty acid ester (Arlacel 481) | 1.300 |
| Polyoxyethylen fatty acid ester (Arlacel 989) | 3.700 |
| Neutral Oil (Miglyol) | 6.000 |
| Paraffin Oil, GP 9 | 14.000 |
| Propylene glycol | 3.800 |
| Magnesium sulphate (MgSO$_4$*7 H$_2$O) | 0.700 |

-continued

|  | % by weight |
|---|---|
| UCA | 0.060 |
| Water demin. | to 100.000 |

EXAMPLE 13

O/W-Emulsion

|  | % by weight |
|---|---|
| PEG 100 Stearate (Arlacel 165) | 5.000 |
| Cetearyl Alcohol (Lanette O) | 3.000 |
| Mineral Oil, GP 9 | 25.000 |
| Paraben mixture | as desired |
| UCA | 0.325 |
| Water demin. | to 100.000 |

EXAMPLE 14

O/W-Emulsion

|  | % by weight |
|---|---|
| Polysorbate-60 (Tween 60) | 3.000 |
| Sorbitan Stearate (Arlacel 60) | 2.000 |
| Cetearyl Alcohol (Lanette O) | 3.000 |
| Mineral Oil, GP 9 | 25.000 |
| Paraben mixture | as desired |
| UCA | 0.035 |
| Water demin. | to 100.000 |

EXAMPLE 15

Cation active Emulsion

|  | % by weight |
|---|---|
| Distearyldimethylammonium chloride (Genamin DS AC) | 5.000 |
| Petroleum jelly, GP 9 | 5.000 |
| Isopropyl palmitate | 2.000 |
| Cetyl alcohol | 1.000 |
| Silicone Oil | 0.100 |
| Propylparaben | 0.100 |
| Methylparaben | 0.100 |
| Glycerol | 4.000 |
| UCA | 0.090 |
| Water demin. | to 100.000 |

EXAMPLE 16

Emulsion

|  | % by weight |
|---|---|
| Sodium cetearyl sulphate (Emulgade F) | 6.000 |
| Mineral Oil, GP 9 | 25.000 |
| Paraben mixture | as desired |
| UCA | 0.450 |
| Water demin. | to 100.000 |

EXAMPLE 17

O/W-Emulsion

| | % by weight |
|---|---|
| Stearic acid | 5.000 |
| Cetearyl Alcohol (Lanette O) | 3.000 |
| Mineral Oil, GP 9 | 25.000 |
| Paraben mixture | as desired |
| Triethanolamine | 1.000 |
| UCA | 0.080 |
| Water demin. | to 100.000 |

Evidence of cis-urocaninic acid induced suppression of contact allergy induced by DNFB (dinitrofluorobenzene).

Material and Methods

Experiment (1)

Test animals: Ten naive, syngeneic female mice per group (age: 12–14 weeks) were used as test animals in the experiments.

Urocaninic acid: trans-Urocaninic acid was purchased from Sigma (Munich, Germany). For isomerisation the trans-uracinic acid solution (1% in dd $H_2O$ buffered with NaOH to pH 6.9) was irradiated with an Osram Vitalux lamp (300 W) to get a conversion of 50% of trans-urocaninic acid to cis-Urocaninic acid, controlled by HPLC-analysis.

The solution of cis/trans racemate was passed through a 0.1 pm Millipore filter and formulated in an O/W cream (1 mg urocaninic acid /ml cream) within the aqueous phase. The O/W-formulation without urocaninic acid served as control.

Induction and elicitation of contact allergy to DNFB

DNFB purchased from Sigma (Munich, Germany) was used as allergen to induce contact allergy (delayed type hypersensitivity (DH) reaction. Before sensibilisation with DNFB 10 mice per group were treated daily about a period of 3 days with 100 µl urocaninic acid cream (group A) respectively with 100 µl placebo cream (group B) on shaved abdominal skin areas (6 $cm^2$).

5 hours after the last topical application of cream mice of both groups were sensitized by epicutaneous treatment on the shaved abdominal skin areas with 30 µl of DNFB (0.6%) soluted in aceton/olive oil (4:1).

8 days later the mice of group A were embrocated on the surface of one ear with 10 µl of urocaninic acid cream (data group A II) and on the surface of the other ear with 10 µl placebo cream (data group A I). Additionally the mice of group B were embrocated on the surface of one ear with 10 µl of urocaninic acid cream (data group B II) and on the other ear with 10 µl placebo cream (data group B I). The distribution of the ears treated with cream (left or right) was statistically randomized in each animal group.

One day later the thickness of both ears in all groups were measured with a micrometer to determine the basic values. Thereafter all mice were challenged with 20 µl DNFB (0.5%) on the surface of both ears and 24 hours later ear thickness was remeasured.

The DH response was calculated as the average of increase in ear thickness per mouse (net ear swelling). The percentage of DH suppression was calculated for ears treated with and without active agent (=cis-urocaninic acid) according to the formula:

$$DH \text{ suppression} = 100 - \frac{100 * \text{net ear swelling (group } A)}{\text{net ear swelling (group } B)} \quad (\%)$$

The statistical significance of data was calculated by the Wilcoxon U-test.

Results (shown in Tab. 1)

The arithmetical mean values of ear thickness were not statistically different in both groups of mice before DNFB challenge. However, 24 hours after DNFB challenge the ear thickness in data group B I (vis. Tab. 1) was significantly encreased in comparison with the data groups A I and B II.

These data give good evidence that either prophylactic treatment with cis-urocaninic acid containing formulations or, in case of sensibilization has already occurred, the treatment with cis-urocaninic acid containing formulations before repeated allergen contact give protection from DH-reaction.

Tab.1: Effect of O/W-creams formulated with or without urocaninic acid on DH response against DNFB

| data group | on days 1–3 treated with (abdomen) | on day 11 treated with (ear) | ear swelling day 13 |
|---|---|---|---|
| A I | active agent | placebo | 7.96 (0.90) |
| A II | active agent | active agent | 4.95 (0.98) |
| B I | placebo | placebo | 11.87 (1.07) |
| B II | placebo | active agent | 7.33 (0.57) | active agent = cream containing urocaninic acid = Formulation A
placebo = cream not containing urocaninic acid = Formulation B Ear swelling was measured in brackets are standard deviations of the mean values.

The ratios of the groups (suppression of ear swelling in %) are:

| A I:B I | = 32.1% |
| A II:A I | = 37.9% |
| A II:B I | = 58.3% |
| A II:B II | = 32.5% |
| B II:A I | = 8.0% |
| B II:B I | = 38.3% |

Experiment (2)

Test animals: As in Experiment (1).

Urocaninic acid: As in Experiment (1). The solution of cis/trans racemate was passed through a 0.1 µm Millipore filter and formulated in an O/W cream (1 mg urocaninic acid/ml cream) within the aqueous phase. The cream additionally contained 0.75% by weight of gamma-linoleic acid.

The O/W-formulation without urocaninic acid but containing gamma-linoleic acid served as control.

Induction and elicitation of contact allergy to DNFB

Before sensibilisation with DNFB 10 mice per group were treated daily about a period of 3 days with 100 µl urocaninic acid cream (group C) respectively with 100 µl placebo cream (group D) on shaved abdominal skin areas (6 $cm^2$).

5 hours after the last topical application of cream mice of both groups were sensitized by epicutaneous treatment on the shaved abdominal skin areas with 30 μl of DNFB (0.6%) soluted in aceton/olive oil (4:1).

8 days later the mice of group C were embrocated on the surface of one ear with 10 μl of urocaninic acid cream (data group C II) and on the other ear with 10 μl placebo cream (data group C I). Additionally the mice of group D were embrocated on the surface of one ear with 10 μl of urocaninic acid cream (data group D II) and on the other ear with 10 μl placebo cream (data group D I). The distribution of the ears treated with cream (left or right) was statistically randomized in each animal group.

One day later the thickness of both ears in all groups were measured with a micrometer to determine the basic values. Thereafter all mice were challenged with 20 μl DNFB (0.5%) on the surface of both ears and 24 hours later ear thickness was remeasured.

The DH response was calculated as the average of increase in ear thickness per mouse (net ear swelling). The percentage of DH suppression was calculated for ears treated with and without active agent according to the formula:

$$DH \text{ suppression} = 100 - \frac{100 * \text{net ear swelling (group } C)}{\text{net ear swelling (group } D)} \quad (\%)$$

The statistical significance of data was calculated by the Wilcoxon U-test.

Results (shown in Tab. 2)

The arithmetical mean values of ear thickness were not statistically different in both groups of mice before DNFB challenge. However, 24 hours after DNFB challenge the ear thickness in data group D I (vis. Tab. 1) was significantly encreased in comparison with the data groups C I and D II.

These data give good evidence that either prophylactic treatment with cis-urocaninic acid containing formulations or, in case of sensitation has already occurred, the treatment with cis-urocaninic acid containing formulations before repeated allergen contact give protection from DH-reaction.

Tab.2: Effect of O/W-creams formulated with or without urocaninic acid on DH response against DNFB

| data group | on days 1–3 treated with (abdomen) | on day 11 treated with (ear) | ear swelling day 13 |
|---|---|---|---|
| C I | active agent | placebo | 7.74 (0.87) |
| C II | active agent | active agent | 4.02 (1.02) |
| D I | placebo | placebo | 11.70 (1.01) |
| D II | placebo | active agent | 6.99 (0.70) | active agent = cream containing urocaninic acid = Formulation C
placebo = cream not containing urocaninic acid = Formulation D Ear swelling was measured in mm * $10^{-2}$. The values in brackets are standard deviations of the mean values.

The ratios of the groups (suppression of ear swelling in %) are:

| A I:B I | = | 33.8% |
|---|---|---|
| A II:A I | = | 48.1% |
| A II:B I | = | 65.6% |
| A II:B II | = | 42.5% |
| B II:A I | = | 9.7% |
| B II:B I | = | 40.3% |

Experiment (3)

Test on antiinflammatory activity

After UV-irradiation (Sol 3, Hönle, Germany) the irradiated skin (area of the irradiated skin 1.0 * 1.2 cm$^2$) was treated with the test formulations.

(1) Test formulation A was applied on 14 volunteers (average age: 13,2 years, standard deviation 7,6 years) immediately after UV irradiation and a second time 6 hours after irradiation. The cream was weighed, thus the applied quantity was 2 mg/cm$^2$.

(2) Test formulation B was applied on 14 volunteers, immediately after UV irradiation and a second time 6 hours after irradiation. The cream was weighed, thus the applied quantity was 2 mg/cm$^2$.

(3) Test formulation C was applied on 14 volunteers, immediately after UV irradiation and a second time 6 hours after irradiation. The cream was weighed, thus the applied quantity was 2 mg/cm$^2$.

(4) Test formulation D was applied on 14 volunteers, immediately after UV irradiation and a second time 6 hours after irradiation. The cream was weighed, thus the applied quantity was 2 mg/cm$^2$.

Results

The induced erythemas were evaluated visually, 24 hours after irradiation:

(a) 12 persons: weak erythema, 2 persons: distinct erythema (b) 13 persons: distinct erythema, 1 person: weak erythema (c) 13 persons: no erythema, 1 person: weak erythema (d) 10 persons: distinct erythema, 3 persons: weak erythema, 1 person : severe erythema Experiment (4)

An O/W-cream according to formulation E (active agent) was applied over a period of 3 days, once a day, to the left volar forearm of a volunteer suffering from nickel allergy and an O/W-cream according to formulation F (placebo) was applied to his right volar forearm. Immediately after the last application both forearms were challenged with 20 μl of a NiSO$_4$-mixture 0.1% in vaseline. The reactions were evaluated visually 72 hours after application of the allergen. Whereas the placebo-treated forearm showed a distinct allergic reaction, the forearm treated with active agent revealed only slight erythema.

Experiment (5)

A volunteer suffering from psoriasis was treated twice a day over a period of six weeks with (5.1) a composition according to formulation A in the region of the left elbow (5.2) a composition according to formulation B in the region of the right elbow.

Both elbows revealed symptoms of psoriasis before the experiment.

Results

After six weeks, the symptoms of psoriasis had been reduced on the left elbow. On the right elbow no change could be noticed.

Experiment (6)

A volunteer suffering from severe psoriasis was treated twice a day over a period of six weeks with (6.1) a composition according to formulation C in the region of the left elbow (6.2) a composition according to formulation D in the region of the right elbow.

Both elbows revealed severe symptoms of psoriasis before the experiment.

Results

After six weeks, the symptoms of psoriasis had been reduced on the left elbow. On the right elbow no change could be noticed.

Formulations according to Experiments (1)–(6)

The active agent containing cream A had the formula

| Ceteareth-20 | 3,00 |
| Cetylstearylalcohol | 8,00 |
| Vaseline | 10,00 |
| Mineral Oil | 10,00 |
| UCA | 1,00 |
| Water demin. | 68,00 |

The placebo B had the formula

| Ceteareth-20 | 3,00 |
| Cetylstearylalcohol | 8,00 |
| Vaseline | 10,00 |
| Mineral Oil | 10,00 |
| Water demin. | 69,00 |

The active agent containing cream C had the formula

| Ceteareth-20 | 3,00 |
| Cetylstearylalcohol | 8,00 |
| Vaseline | 10,00 |
| Mineral Oil | 10,00 |
| UCA | 1,00 |
| gamma-linolenic acid | 0,75 |
| Water demin. | 67,25 |

The placebo D had the formula

| Ceteareth-20 | 3,00 |
| Cetylstearylalcohol | 8,00 |
| Vaseline | 10,00 |
| Mineral Oil | 10,00 |
| gamma-linolenic acid | 0,75 |
| Water demin. | 68,25 |

The active agent containing cream E had the formula

| Ceteareth-20 | 3,00 |
| Cetylstearylalcohol | 8,00 |
| Vaseline | 10,00 |
| Mineral Oil | 10,00 |
| UCA | 2,00 |
| Water demin. | 67,00 |

The placebo F had the formula

| Ceteareth-20 | 3,00 |
| Cetylstearylalcohol | 8,00 |
| Vaseline | 10,00 |
| Mineral Oil | 10,00 |
| Water demin. | 69,00 |

We claim:

1. A method for the treatment of a human patient afflicted with neurodermatitis, which comprises topically administering to such patient an amount effective for treating such neurodermatitis of cis-urocanic acid or a salt thereof.

2. The method according to claim 1, wherein this cis-urocanic acid or salt thereof is applied as a composition also containing a diluent.

3. The method according to claim 2, wherein the composition contains about 0.0001 mg/ml–60 mg/ml of the cis-urocanic acid or salt thereof.

4. The method according to claim 2, wherein the composition further contains about 0.2–2% by weight of an unsaturated fatty acid ester or salt thereof.

5. The method according to claim 1, wherein the cis-urocanic acid or salt thereof is applied in admixture with trans-urocanic acid or salt thereof.

6. The method according to claim 1, wherein the cis-urocanic acid or salt thereof is applied as a racemic mixture with trans-urocanic acid or salt thereof.

* * * * *